US012622658B2

(12) United States Patent (10) Patent No.: US 12,622,658 B2
Pfister                                            (45) Date of Patent: May 12, 2026

(54) ACTUATION METHOD FOR X-RAY DEVICE AND X-RAY DEVICE

(71) Applicant: Siemens Healthcare GmbH, Erlangen (DE)

(72) Inventor: Marcus Pfister, Bubenreuth (DE)

(73) Assignee: Siemens Healthineers AG, Forchheim (DE)

( * ) Notice: Subject to any disclaimer, the term of this patent is extended or adjusted under 35 U.S.C. 154(b) by 699 days.

(21) Appl. No.: 18/084,531

(22) Filed: Dec. 19, 2022

(65) Prior Publication Data

US 2023/0190212 A1 Jun. 22, 2023

(30) Foreign Application Priority Data

Dec. 20, 2021 (DE) ..................... 10 2021 214 738.0

(51) Int. Cl.
A61B 6/06 (2006.01)
A61B 6/00 (2024.01)
A61B 6/46 (2024.01)

(52) U.S. Cl.
CPC ................ A61B 6/06 (2013.01); A61B 6/461 (2013.01)

(58) Field of Classification Search
CPC .. A61B 6/06; A61B 6/461; A61B 6/54; A61B 6/4441; A61B 6/487; A61B 6/12
See application file for complete search history.

(56) References Cited

U.S. PATENT DOCUMENTS

2009/0150184 A1* 6/2009 Spahn .................... G16H 30/20
                                                      705/2
2018/0055379 A1* 3/2018 Redel .................... G16H 50/30
                        (Continued)

FOREIGN PATENT DOCUMENTS

DE     102008049695 A1    4/2010
EP          3656309 A1    5/2020

OTHER PUBLICATIONS

Alhrishy, Mazen, et al. "A machine learning framework for context specific collimation and workflow phase detection." Proc. 15th Int. Symp. Comput. Methods Biomechanics and Biomedical Eng. 3rd Conf. Imaging Visualization (CMBBE 2018). 2018. pp. 1-10.
                        (Continued)

*Primary Examiner* — Iriana Cruz
(74) *Attorney, Agent, or Firm* — Lempia Summerfield Katz LLC

(57) ABSTRACT

A method for automatic actuation of an X-ray device includes acquiring at least one X-ray image of a body containing at least two objects and/or an object divisible into at least two object sections, segmenting and classify the at least two objects and/or the at least two object sections of the object, and determining an immediately upcoming or current workflow step of the intervention. Information relating to objects or object sections relevant to the determined workflow step is retrieved, at least one object of the at least two objects or at least one object section of the at least two object sections of the object is selected taking the information into account, and a collimator of the X-ray device is automatically adjusted for overlaying the selected object or selected object section taking the information into account. At least one X-ray image is acquired using the thus adjusted collimator and displayed.

17 Claims, 5 Drawing Sheets

(56)　　　　　References Cited

U.S. PATENT DOCUMENTS

| | | | |
|---|---|---|---|
| 2018/0129896 A1 | 5/2018 | Wu et al. | |
| 2020/0074223 A1* | 3/2020 | Cho | G06F 18/214 |
| 2022/0108540 A1* | 4/2022 | Lamash | G06T 19/20 |
| 2022/0175269 A1* | 6/2022 | Lu | A61B 5/6851 |
| 2023/0148985 A1* | 5/2023 | Kanno | A61B 6/545 |
| | | | 378/62 |
| 2023/0329651 A1* | 10/2023 | Boxall | A61B 6/102 |
| 2024/0298995 A1* | 9/2024 | Flexman | A61B 6/06 |

OTHER PUBLICATIONS

Arbogast, Nikolaus, et al. "Workflow Phase Detection in Fluoroscopic Images Using Convolutional Neural Networks." Bildverarbeitung für die Medizin 2019. Springer Vieweg, Wiesbaden, 2019. 191-196.
Breininger, Katharina, et al. "Multiple device segmentation for fluoroscopic imaging using multi-task learning." Intravascular imaging and computer assisted stenting and large-scale annotation of biomedical data and expert label synthesis. Springer, Cham, 2018. 19-27.
Kerstin Siebarth, et al. Siemens, "Dynamic x-ray collimation on the basis of an overlaying of a segmented volume" 2015.
Ma, YingLiang, et al. "Real-time guiding catheter and guidewire detection for congenital cardiovascular interventions." International Conference on Functional Imaging and Modeling of the Heart. Springer, Cham, 2017. pp. 172-182.
Padoy, Nicolas. "Machine and deep learning for workflow recognition during surgery." Minimally Invasive Therapy & Allied Technologies 28.2 (2019): 1-10.

* cited by examiner

Figure 6:
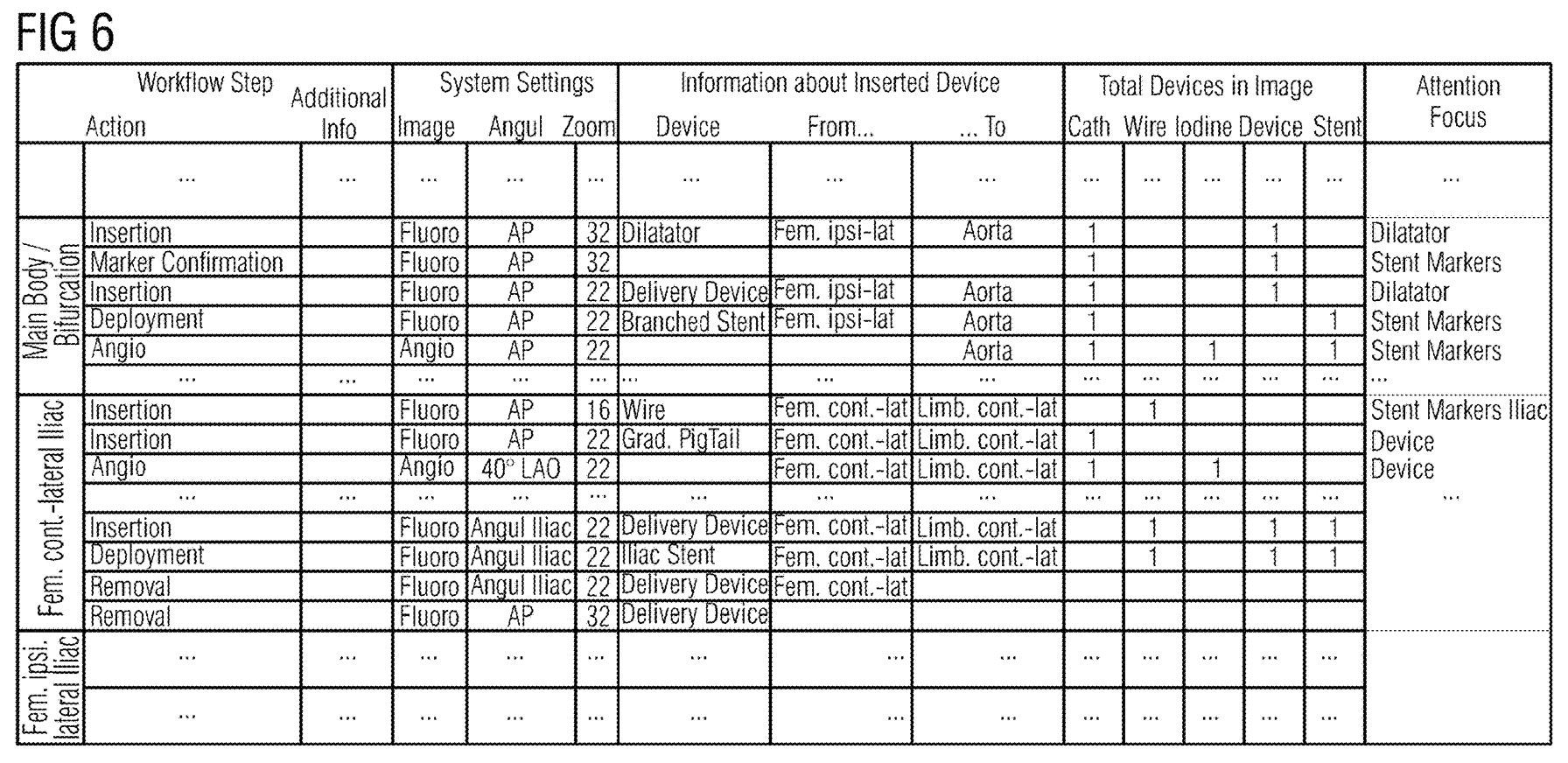

| | Workflow Step | | System Settings | | | Information about Inserted Device | | | Total Devices in Image | | | | | Attention Focus |
|---|---|---|---|---|---|---|---|---|---|---|---|---|---|---|
| | Action | Additional Info | Image | Angul | Zoom | Device | From... | ...To | Cath | Wire | Iodine | Device | Stent | Focus |
| | ... | ... | ... | ... | ... | ... | ... | ... | ... | ... | ... | ... | ... | ... |
| Main Body / Bifurcation | Insertion | | Fluoro | AP | 32 | Dilator | Fem. ipsi-lat | Aorta | 1 | | | 1 | | Dilator |
| | Marker Confirmation | | Fluoro | AP | 32 | | | | 1 | | | 1 | | Stent Markers |
| | Insertion | | Fluoro | AP | 22 | Delivery Device | Fem. ipsi-lat | Aorta | 1 | | | 1 | | Dilator |
| | Deployment | | Fluoro | AP | 22 | Branched Stent | Fem. ipsi-lat | Aorta | 1 | | | | 1 | Stent Markers |
| | Angio | | Angio | AP | 22 | | | Aorta | 1 | | 1 | | 1 | Stent Markers |
| | ... | | ... | ... | ... | ... | ... | ... | ... | ... | ... | ... | ... | ... |
| Fem. cont.-lateral Iliac | Insertion | | Fluoro | AP | 16 | Wire | Fem. cont.-lat | Limb. cont.-lat | 1 | 1 | | | | Stent Markers Iliac |
| | Insertion | | Fluoro | AP | 22 | Grad. PigTail | Fem. cont.-lat | Limb. cont.-lat | 1 | 1 | | | | Device |
| | Angio | | Angio | 40° LAO | 22 | | Fem. cont.-lat | Limb. cont.-lat | 1 | | 1 | | | Device |
| | ... | | ... | ... | ... | ... | ... | ... | ... | ... | ... | ... | ... | ... |
| | Insertion | | Fluoro | Angul Iliac | 22 | Delivery Device | Fem. cont.-lat | Limb. cont.-lat | 1 | 1 | | 1 | 1 | |
| | Deployment | | Fluoro | Angul Iliac | 22 | Iliac Stent | Fem. cont.-lat | Limb. cont.-lat | 1 | 1 | | 1 | 1 | |
| | Removal | | Fluoro | Angul Iliac | 22 | Delivery Device | Fem. cont.-lat | | | | | | | |
| | Removal | | Fluoro | AP | 32 | Delivery Device | | | | | | | | |
| | ... | | ... | ... | ... | ... | ... | ... | ... | ... | ... | ... | ... | ... |
| Fem. ipsi.-lateral Iliac | ... | | ... | ... | ... | ... | ... | ... | ... | ... | ... | ... | ... | ... |

ACTUATION METHOD FOR X-RAY DEVICE AND X-RAY DEVICE

This application claims the benefit of German Patent Application No. DE 10 2021 214 738.0, filed on Dec. 20, 2021, which is hereby incorporated by reference in its entirety.

BACKGROUND

The present embodiments relate to automatic actuation of an X-ray device and an X-ray device for performing such a method.

Complex operative interventions and procedures are nowadays very frequently carried out within the framework of new technological developments based a minimally invasive approach (e.g., with image monitoring (fluoroscopy) using large C-arm X-ray devices, such as EVAR procedures by angiography systems). Also included therein are procedures in which a robotic system provided for moving objects (e.g., stents, catheters, guidewires, etc.) in the body of a patient is introduced between the hands of the treating practitioner and the patient (e.g., the Corindus CorPath GRX® system). The operational sequences and workflows associated with these complex interventions are likewise increasingly more complex, while the patient's exposure to radiation also increases with the length of the procedures.

To provide support in complex workflows, systems that display the respective workflow step are known. Some of these methods recognize the respective workflow step automatically (e.g., from video images ("Machine and deep learning for workflow recognition during surgery" by N. Padoy, Minimally Invasive Therapy & Allied Technologies, Volume 28, 2019, p. 1ff.) or from X-ray images ("Workflow Phase Detection in Fluoroscopic Images Using Convolutional Neural Networks" by N. Arbogast et al., Bildverarbeitung für die Medizin (*Image processing for medicine*), 2019)).

The choice of appropriate acquisition parameters (e.g., tube voltage or image frequency) is important in order to minimize the exposure to radiation for the patient and medical staff during the lengthy procedures, but the correct deployment of a collimator when collimating the irradiated field of view (FoV) is also important. In this connection, proposals for automatic collimation are known, for example, based on registered volumes (e.g., unexamined German application DE 10 2008 049 695 A1) or based on the totality of the detected objects ("A Machine Learning Framework for Context Specific Collimation and Workflow Phase Detection" by M. Alhrishy et al., 15th International Symposium on Computer Methods in Biomechanics and Biomedical Engineering, 2018). However, these approaches are of limited benefit for many procedures (e.g., complex aortic procedures) since the introduced objects (e.g., stents, catheters, guidewires, etc.) fill out the major part of the uncollimated X-ray image, and consequently, the collimation is not specific enough to significantly reduce the radiation exposure.

Otherwise, a collimation is typically carried out by an operator (e.g., physician) by manually introducing the diaphragm elements of the collimator based on the current situation shown in the X-ray image. This is time-consuming and leads to an interruption of the clinical workflow. Further, the procedure is non-reproducibly dependent on the particular operator since the particular operator is first to manually identify a region of interest (RoI) around which the collimation is then applied.

SUMMARY AND DESCRIPTION

The scope of the present invention is defined solely by the appended claims and is not affected to any degree by the statements within this summary.

The present embodiments may obviate one or more of the drawbacks or limitations in the related art. For example, within the scope of X-ray monitoring of interventional procedures, a method that provides that an operator may concentrate on the respective workflow step without distraction is provided. As another example, an X-ray device suitable for performing the method is provided.

A method of the present embodiments for automatic actuation of an X-ray device during a medical intervention including at least two workflow steps on a body of a patient containing at least two objects and/or containing one object that is divisible into at least two object sections includes acquiring at least one X-ray image of the body containing the at least two objects and/or the object divisible into at least two object sections. The method also includes segmenting and classifying the at least two objects and/or of at least two object sections of the object, determining the immediately upcoming or current workflow step of the intervention, and retrieving information relating to objects or object sections relevant to the particular workflow step. The method also includes selecting at least one object of the at least two objects or at least one object section of the at least two object sections of the object taking the information into account. The method includes automatically adjusting a collimator of the X-ray device for overlaying the selected object or selected object sections taking the information into account, and acquiring and displaying at least one X-ray image using the thus adjusted collimator. When complex medical interventions are carried out under X-ray monitoring, the method according to the present embodiments enables an operator (e.g., physician) to concentrate on performing the intervention without having to deal in addition with controlling the collimator in order to limit the overlay region. This provides there is less distraction and, as a result, makes for a faster and error-free performance of the intervention. Further, by limiting the overlay to the actually relevant section, the exposure to radiation for the patient and possibly the operator(s) is reduced to a minimum. Medical procedures are rendered less stressful for patient and medical staff as a result.

For example, the X-ray images are formed at least to some extent by fluoroscopic X-ray images. Thus, among the X-ray images acquired using collimation and displayed for live X-ray monitoring of the intervention, series of fluoroscopic X-ray images may be acquired and played back. The X-ray image(s) initially acquired as an overview containing the object(s) in the body of the patient may be, for example, a 2D or 3D X-ray image or also a series of fluoroscopic X-ray images.

The method is suitable for a number of complex interventions using X-ray monitoring (e.g., also for minimally invasive interventions using robot-assisted navigation). Basically, robotic systems by which an automatic advancement (e.g., a semi-automatic advancement) of an object (e.g., catheter and/or guidewire) in a hollow organ of a patient may be effected with robotic assistance (e.g., Corindus CorPath GRX system) are known. For this purpose, the treating practitioner is provided with a corresponding user interface for initiating the remotely controlled movements, and fluoroscopic images are acquired and displayed to the operator to provide the necessary visual feedback.

Beneficially, the objects used for the intervention are formed by instruments, catheters, implants, or guidewires. Further, a contrast agent may also be used as an object.

Many methods for automatic segmentation are known (e.g., pixel-, edge- and region-oriented methods), as well as model- and texture-based methods. According to a further embodiment, the segmentation and/or classification (e.g., identification and categorization) of the objects is performed by at least one machine-learning algorithm. Such algorithms are described, for example, in the article "Real-time guiding catheter and guidewire detection for congenital cardiovascular interventions," by Y. Ma et al., Int. Conf. Funct. Imaging Model. Hear., 2017, pp. 172-182. By using machine-learning algorithms, it is possible to perform segmentations and classifications in a particularly precise, reliable, and rapid manner. The machine-learning algorithms may be trained based on a number of examples.

According to a further embodiment, the immediately upcoming or current workflow step is determined automatically (e.g., by a machine-learning algorithm) or using a user query. Here too, methods are known for automatically recognizing workflow steps (e.g., from video images ("Machine and deep learning for workflow recognition during surgery" by N. Padoy, Minimally Invasive Therapy & Allied Technologies, Volume 28, 2019, p. 1ff.) or from X-ray images ("Workflow Phase Detection in Fluoroscopic Images Using Convolutional Neural Networks" by N. Arbogast et al., Bildverarbeitung für die Medizin (*Image processing for medicine*), 2019)). Machine-learning algorithms are particularly well suited for a precise detection of the respective workflow step. The algorithms may be trained in advance with the aid of a number of examples. Alternatively, it is also possible to query a user input that may then be input by an operator, for example, using an input unit (e.g., keyboard, smart device, voice input device, etc.). It is also possible to retrieve, for example, upcoming workflow steps from tables or to use a feedback message from an organ program.

According to an embodiment, the retrieved information relating to objects or object sections relevant to the determined workflow step includes an indication of which object (s) or which object section(s) are relevant to the respective workflow step. If more than one object or object section is relevant, a prioritization of the objects or object sections may also be specified. The information may be retrieved, for example, from a memory unit or from a database. The information may be stored there in various formats (e.g., in the form of a list or a lookup table). Thus, there may be listed in such a table for an endovascular aortic aneurysm repair (EVAR) procedure relating to a first workflow step "Insert Objects" (Insertion), for example, a device known as a dilatator (e.g., tool for dilating the vascular access) as the relevant object onto which the focus of the collimator is to be directed. For a second workflow step "Marker Confirmation", localizing aids known as stent markers are the relevant objects, etc.

According to a further embodiment, the collimator of the X-ray device is set taking the information into account such that essentially only the at least one relevant object or the at least one relevant object section are inserted. Non-relevant objects and the background may therefore be partially or completely masked out, for example. In this way, the operator may concentrate fully on the relevant object without being distracted by additional objects. Generally, a collimator may be set, for example, by automatic insertion of adjustable diaphragm elements or filters such that only specific regions are visible on an X-ray image. Suitable collimators for this are well-known.

According to a further embodiment, the collimator of the X-ray device is set taking the information into account such that a minimum bounding rectangle (e.g., a bounding box) is projected as an overlay that contains the whole of the at least one relevant object or the at least one relevant object section. A minimum bounding rectangle of the type may be easily determined, for example, by a calculation unit using a mathematical algorithm. A minimum bounding rectangle is also easily insertable by a low-complexity collimator. Alternatively, a minimum bounding circular or oval shape may also be inserted. In cases in which an assignment to the surroundings is important, or also generally depending on a preference of the operator, a peripheral region (e.g., adjustable or selectable in advance by the operator) may be inserted in addition to the minimum bounding rectangle or the bounding box.

According to a further embodiment, the method is repeated depending on the progress of the intervention, triggered by the start of a new workflow step, at regular time intervals, or user-triggered. By a regular or triggered repetition, it may be provided that the exposure to radiation is kept to a minimum during the entire intervention. A triggering by the start of a new workflow step may be provided, for example. In this case, an acquisition (e.g., overview acquisition) of at least one X-ray image and a corresponding segmentation and classification of the at least two objects and/or of the at least two object sections of the object may subsequently be performed, and information relating to objects or object sections relevant to the workflow step may be retrieved. The relevant object or the relevant object section is then selected and inserted by the collimator, and at least one X-ray image is acquired and displayed. This may be repeated at each further change of workflow step.

The present embodiments also include an X-ray device for performing an above-described method, having an acquisition system including an X-ray detector and an X-ray source for acquiring X-ray images. The X-ray device also includes an image processing unit for processing X-ray images using at least one algorithm for segmenting and classifying objects. The X-ray device includes a collimator for inserting image sections, and a determination unit for detecting the current or upcoming workflow step. The X-ray device also includes a calculation unit for retrieving information relating to objects relevant to the upcoming or current workflow step, and a selection unit for selecting at least one object or object section taking the information into account. The X-ray device includes an input unit for receiving user inputs, a memory unit for storing data, a display unit for displaying X-ray images, and a system control unit for actuating the X-ray device. The system control unit may also combine the determination unit, the calculation unit, and the selection unit within itself, for example in the form of a calculation unit with processor.

According to a further embodiment, the X-ray device is assigned a robotic system including at least one robot control unit and a robot-assisted drive system having a drive and a drive mechanism. The drive system is configured to move at least one medical object in a hollow organ of a patient based on control signals of the robot control unit.

BRIEF DESCRIPTION OF THE DRAWINGS

FIG. 4 shows a further view of an example of an X-ray image containing a displayed bounding box for overlaying a relevant object section from a plurality of objects;

FIG. 6 shows an example of a table containing stored information relating to the workflow steps of an EVAR procedure.

DETAILED DESCRIPTION

Figure 1:
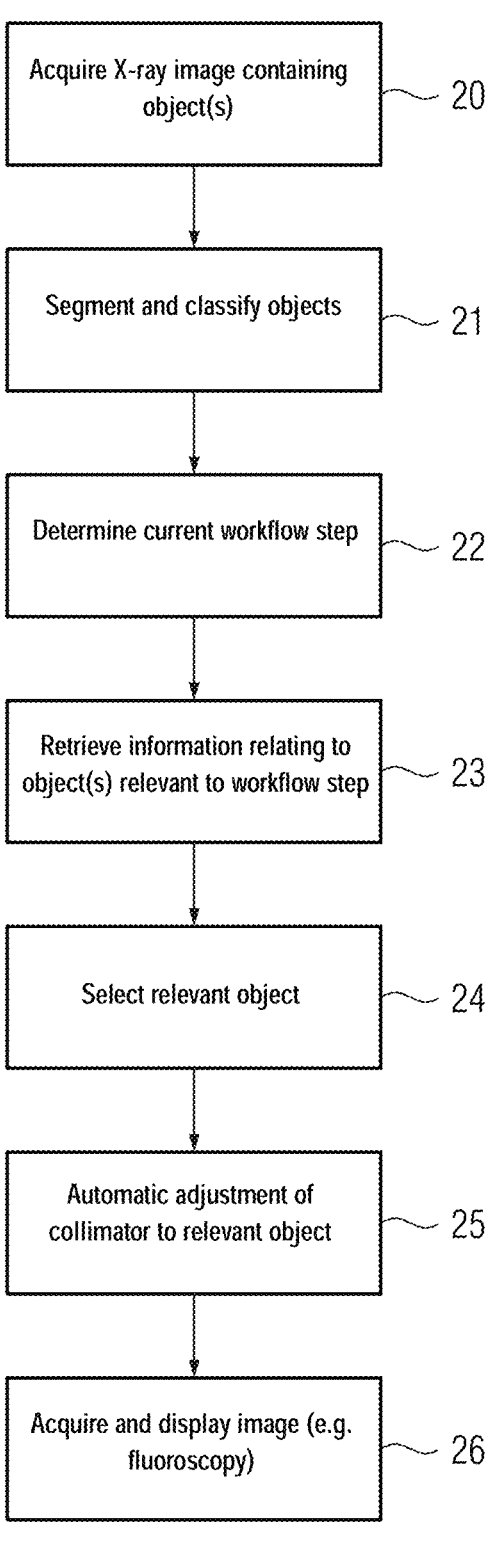
FIG. 1 shows a view of acts of a method according to the present embodiments.

FIG. 1 shows a sequence of acts of one embodiment of a method for automatic actuation of an X-ray device. The method may be performed, for example, during an interventional procedure on a body of a patient, such as, for example, an endovascular aortic aneurysm repair (EVAR). In principle, the method may be applied to all interventional procedures under X-ray monitoring having at least two objects and/or having an object divisible into at least two object sections (e.g., during interventions on coronary blood vessels, interventions in interventional radiology, or neuroradiology). The method may be used, for example, also for minimally invasive interventions using robot-assisted navigation. Basically, robotic systems by which an object (e.g., a catheter and/or guidewire) may be advanced in a hollow organ of a patient in a robotically assisted (semi-)automatic manner (e.g., Corindus CorPath GRX system) are known. For this purpose, a corresponding user interface is made available to the treating practitioner for initiating the remotely controlled movements, and fluoroscopic images are acquired and displayed to the operator to provide the necessary visual feedback.

Basically, the method according to the present embodiments includes an automatic dynamic collimation based on the combined use of the information from a segmentation and classification of the different objects visible in the X-ray image and the detailed (e.g., stored) information relating to the respective current workflow step (e.g., which object in the respective workflow step is relevant and is used or on which object section the attention focus lies, such as stent marker, guidewire tip, etc.). Thus, the object(s) or object section(s) used in the current workflow step are intended to be "visible" to an operator (e.g., physician), but the surroundings are largely or entirely masked out.

In a first act 20, at least one X-ray image of the body containing the at least two objects and/or the object divisible into at least two object sections is acquired. The acquired image may be an 2D X-ray image or a 3D X-ray image. One or more fluoroscopic X-ray images may also be acquired. What is important here is that at least one object consisting of a plurality of object sections or a plurality of objects that are or could be relevant to the workflow steps of the intervention are imaged on the X-ray image.

In a second act 21, the X-ray image is segmented, and the segmented X-ray image is classified with regard to the at least two objects and/or the at least two object sections of the object (e.g., it is identified which object(s) is (are) concerned). A number of methods for automatic segmentation are known (e.g., pixel-, edge-, and region-oriented methods as well as model- and texture-based methods). By the classification, the corresponding object or objects and/or the corresponding object sections are then recognized or identified. It is also possible to use, for example, one or more machine-learning algorithms for the segmentation and/or classification. Such algorithms are described, for example, in the article "Real-time guiding catheter and guidewire detection for congenital cardiovascular interventions" by Y. Ma et al., Int. Conf. Funct. Imaging Model. Hear., 2017, pp. 172-182.

In a third act 22, the immediately upcoming or current workflow step of the intervention is determined. This may be achieved automatically (e.g., by a machine-learning algorithm) or also by a user query. An automatic recognition of the respective workflow step may be obtained, for example, from video images (e.g., "Machine and deep learning for workflow recognition during surgery," by N. Padoy, Minimally Invasive Therapy & Allied Technologies, Volume 28, 2019, p. 1ff.) or from X-ray images (e.g., "Workflow Phase Detection in Fluoroscopic Images Using Convolutional Neural Networks" by N. Arbogast et al., Bildverarbeitung für die Medizin (*Image processing for medicine*), 2019). Machine-learning algorithms are well suited for a precise detection of the respective workflow step. These may be trained in advance based on a number of examples. Alternatively, it is also possible to query a user input that may then be input by an operator, for example, by an input unit (e.g., keyboard, smart device, voice input device, etc.). Upcoming workflow steps may also be retrieved, for example, from tables or organ programs.

The order of acts 20 to 23 does not necessarily have to be as described above. For example, the third act 22 may also be performed before the first act 20 and the second act.

In a fourth act 23, information relating to objects or object sections relevant to the determined workflow step is retrieved. The retrieved information contains at least one indication of which object(s) or which object section(s) are relevant to the respective workflow step. If more than one object or object section is relevant, a prioritization of the objects or object sections may also be specified. The information may be retrieved, for example, from a memory unit or from a database. The information may be stored there in various formats (e.g., in the form of a list or a lookup table). Thus, there may be listed in such a table for an endovascular aortic aneurysm repair (EVAR) procedure relating to a first workflow step "Insert Objects" (Insertion), for example, a device known as a dilatator (e.g., tool for dilating the vascular access) as the relevant object onto which the focus of the collimator is to be directed. For a second workflow step "Marker Confirmation", localizing aids known as stent markers are the relevant objects. An exemplary (e.g., not complete) table containing such indications for an EVAR procedure is shown in FIG. 6. The respective workflow steps are listed under "Workflow Step", the respective objects used are listed under "Information about Inserted Device", and the respective relevant object is listed under "Attention Focus".

In a fifth act 24, a selection of at least one object of the at least two objects or at least one object section of the at least two object sections of the object is made (e.g., by a selection unit) taking the information into account. In the above-cited example containing the table in FIG. 6, the dilatator is selected in the first workflow step "Insert Objects" (e.g., Insertion) as the relevant object onto which the focus of the collimator is to be directed. For the second workflow step "Marker Confirmation", the stent markers are selected, etc.

Next, in a sixth act 25, the collimator of the X-ray device used is automatically set, for example, with the aid of the segmented and classified X-ray image such that the selected object or the selected object section is inserted and the background or the non-relevant objects or object sections are largely or entirely masked out. In this way, the operator may concentrate completely, without distraction, on the object relevant at the given point in time. Generally, a collimator may be set, for example, by automatic insertion of adjustable diaphragm elements or filters such that only certain regions are visible on an X-ray image. It is also possible to illuminate (e.g., by a filter of the collimator) the background and/or the non-relevant objects using a very low X-ray dose compared to that used for the relevant object.

It is also possible, for example, to determine and overlay a minimum bounding rectangle (e.g., a bounding box) that contains the whole of the at least one relevant object or the at least one relevant object section. A minimum bounding rectangle of said type may easily be determined, for example, by a calculation unit using a mathematical algorithm. A minimum bounding rectangle may also be inserted by a low-complexity collimator. Alternatively, a minimum bounding circular or oval shape may also be inserted. In cases in which an assignment to the surroundings is important, or also generally depending on a preference of the operator, a peripheral region (e.g., adjustable or selectable in advance by the operator) may be inserted in addition to the minimum bounding rectangle or the bounding box.

Figure 2:
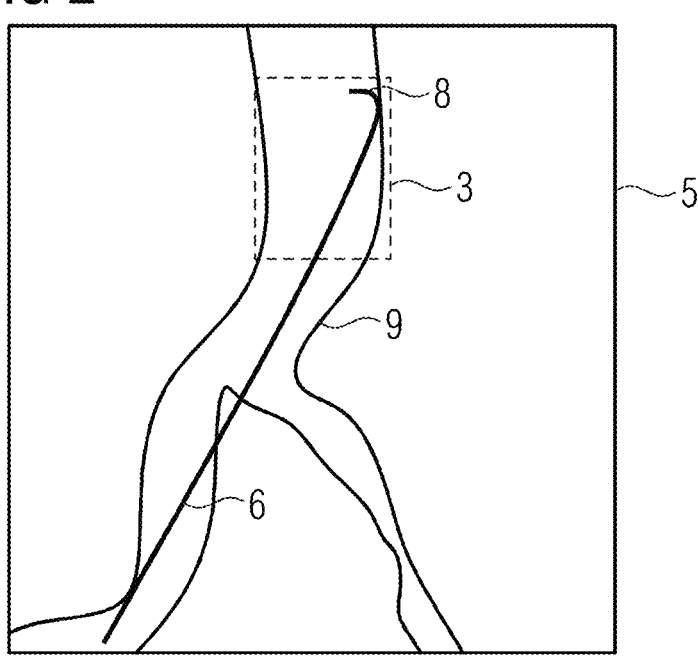
FIG. 2 shows a view of an example of an X-ray image containing a displayed bounding box for overlaying a relevant object section of an object.
Figure 3:
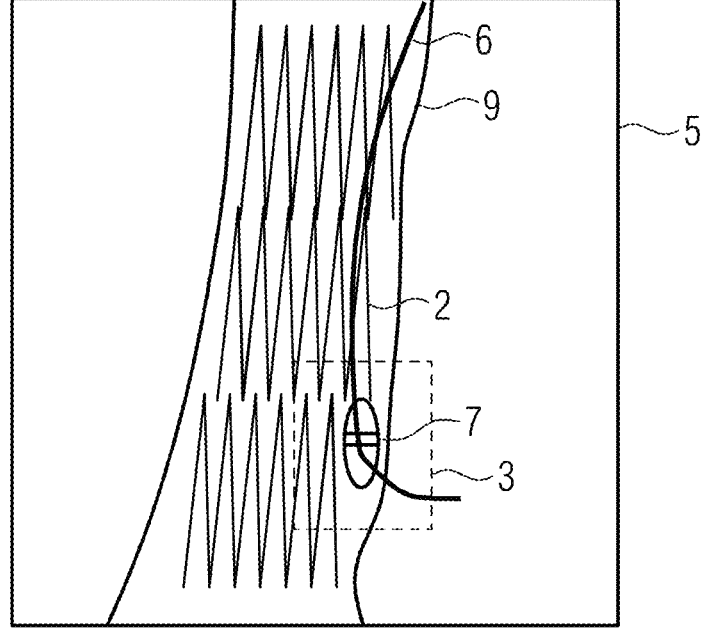
FIG. 3 shows a further view of an example of an X-ray image containing a displayed bounding box for overlaying a relevant object from a plurality of objects.
Figure 4:
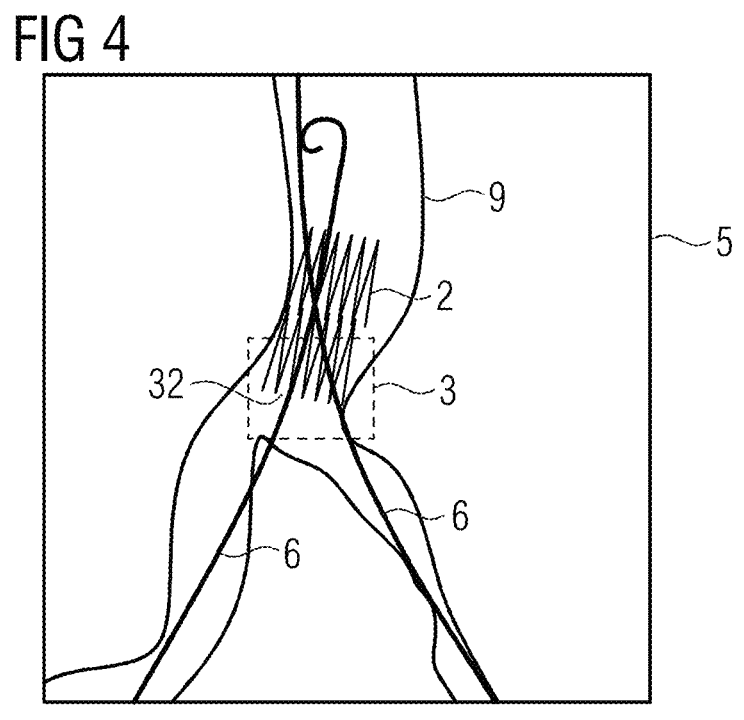

A number of examples of an X-ray image 5 in each case containing a displayed bounding box 3 for overlaying a relevant object or object section are shown in FIGS. 2 to 4. FIG. 2 depicts a hollow organ 9 containing a guidewire 6 on the X-ray image 5. If the information (e.g., the lookup table) indicates that the guidewire tip 8 (e.g., the front 5, 8, or 10 cm of the guidewire 6) forms the relevant object section, a minimum bounding rectangle 3 (e.g., possibly including peripheral region) around the guidewire tip 8 is determined (e.g., by a calculation unit) and inserted accordingly. FIG. 3 shows a stent 2 and a guidewire 6 in a hollow organ 9 on the X-ray image 5. A marker 7 that represents the relevant object section in a workflow step is arranged at an aperture of the stent 2. A minimum bounding rectangle 3 (e.g., possibly including peripheral region) around the marker 7 of the stent 2 is determined (e.g., by a calculation unit) and inserted accordingly. FIG. 4 shows a hollow organ 9 containing two guidewires 6 and a stent 2 having a stent exit 32 on the X-ray image 5. The stent exit 32 (e.g., in an EVAR procedure, iliac) is the relevant object section. A minimum bounding rectangle 3 (e.g., possibly including peripheral region) around the stent exit 32 of the stent 2 is determined (e.g., by a calculation unit) and inserted accordingly.

In a seventh act 26, at least one X-ray image is then acquired and displayed on a display unit. In this case, for example, during an operative intervention and/or a robot-assisted intervention with X-ray monitoring, a series of fluoroscopic X-ray images is acquired and displayed on a monitor to the operator. In this way, the operator may concentrate on the region of the intervention that is important for the current situation.

The method may be repeated depending on the progress of the intervention, triggered by the start of a new workflow step, at regular time intervals or user-triggered (e.g., on demand). A triggering by the start of a new workflow step may be provided, for example. In this case an acquisition (e.g., an overview acquisition) of at least one X-ray image and a corresponding segmentation and classification of the at least two objects and/or of the at least two object sections of the object may subsequently be performed. Information relating to objects or object sections relevant to the workflow step may be retrieved. The relevant object/relevant object section is then selected and inserted using the collimator, and at least one X-ray image is acquired and displayed. This may be repeated at each further change of workflow step. It is also possible to perform a segmentation and classification for each X-ray image (e.g., in the event that the relevant object or the relevant object section is acquired using a full X-ray dose and the surroundings or the remaining objects are acquired using a lower X-ray dose). This may then be used at each change of workflow step in order to select the relevant object or the relevant object section.

Typically, within the scope of many well-known and frequently used interventions, referred to as standard operating procedures (SOPs), there already exists a collection of data (e.g., table or similar) containing various specifications, as shown, for example, in FIG. 6 in the columns "Workflow Step" and "System Settings". As a preparation phase for the method, data collections of the type are correspondingly extended or supplemented by a list of the objects required for this step (e.g., guidewire, catheter, instrument, tool, . . . ) and the corresponding relevant object or object section (e.g., where the attention focus is to be placed, such as a stent marker, guidewire tip, etc.).

In addition, an operator may optionally also select or determine the objects that are to remain visible to him/her (e.g., the stent requiring to be placed) or the objects that may also be masked out (e.g., the supplying guidewires). A warning may also be output if the region of the current collimation deviates sharply from the detected instruments. If a number of objects or object sections are relevant (e.g., two objects) and a prioritization exists, then, for example, the most relevant object may be inserted centrally and the, for example, second most relevant object may be inserted at the boundary.

Figure 5:
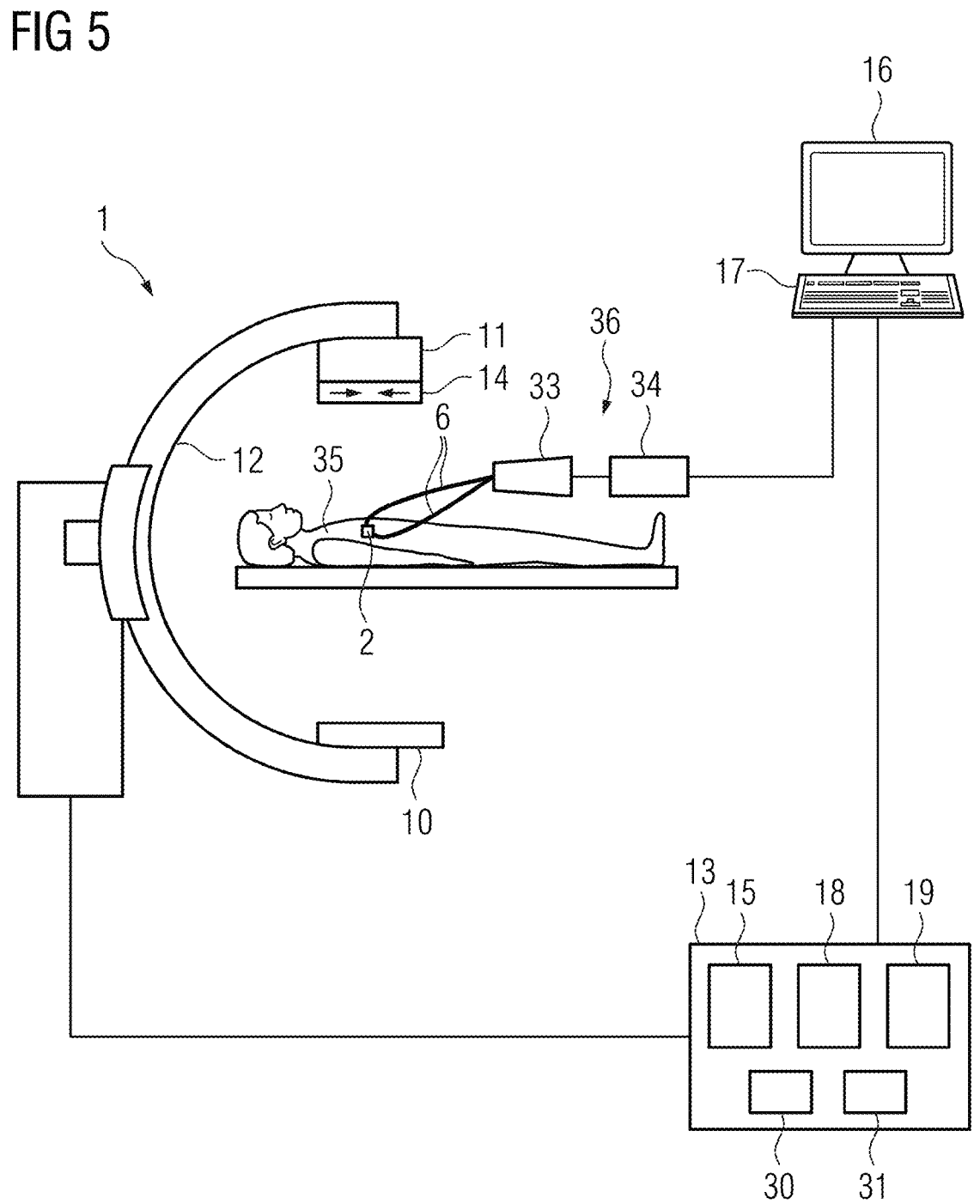
FIG. 5 shows a view of an X-ray device for performing the method according to the present embodiments.

An X-ray device 1 for performing the method is shown in FIG. 5. The X-ray device 1 is also assigned a robotic system 36 for conducting robot-assisted navigation in the body 35 of a patient. The X-ray device 1 has an acquisition system including an X-ray detector 10 and an X-ray source 11 for acquiring X-ray images. Positioned downstream of the X-ray source 11 is a collimator 14 for overlaying image sections by adjusting diaphragm elements and/or filters. The X-ray device 1 also includes an image processing unit 15 for processing X-ray images. This may be configured, for example, for segmenting and classifying objects imaged on X-ray images and, for this purpose, may use, for example, one or more algorithms (e.g., also machine-learning algorithms). The X-ray device also has a determination unit 18 for detecting the current or upcoming workflow step (e.g., also using an algorithm, such as a machine-learning algorithm). It is also possible for an operator to simply evaluate a table or an input. The X-ray device 1 also includes a calculation unit 19 for retrieving information relating to objects relevant to the upcoming or current workflow step; this information may be retrieved as described from a memory unit 31 or from a database. A selection unit 30 then makes a selection of at least one object or object section taking the information from the memory unit 31 or from a database into account. The information is stored, for example, in the form of tables. Also present are an input unit 17 for receiving user inputs (e.g., keyboard, smart device, touchpad, microphone, etc.) and a display unit 16 for displaying X-ray images (e.g., a monitor, projector, or smart device). A communications unit for exchanging data may also be present. The X-ray device is actuated by a system control unit 13. The system control unit 13 may in this case also combine the determination unit 18, the calculation unit 19, and the selection unit 30 within itself (e.g., in the form of a calculation unit with processor).

The robotic system 36 includes at least one robot control unit 34 and a robot-assisted drive system 33 having a drive and a drive mechanism. The drive system 33 is configured to move at least one medical object (e.g., guidewires 6) in a hollow organ of the body 35 of the patient based on control signals of the robot control unit 34. For this, for example, an actuation signal transmitted by an operator via an input unit (e.g., joystick, touchpad, control knob, . . . ) to the robot control unit 34 is used. Using the drive mechanism and the drive, the guidewire 6, for example, may be axially advanced and retracted and/or rotationally moved in addition. Alternatively, the operator may also undertake a path planning process for the object or have the path plan generated automatically. This is transferred to the robot control unit 34, thus enabling a fully automatic movement to be performed. The path planning may also be used as a reference in the case of a semi-automatic movement.

The present embodiments may be briefly summarized as follows: In order to achieve a particularly low exposure to radiation and a particularly smooth and fast implementation, a method for automatic actuation of an X-ray device during a medical intervention including at least two workflow steps on the body of a patient containing at least two objects and/or containing one object that is divisible into at least two object sections is provided. The method includes acquiring at least one X-ray image of the body containing the at least two objects and/or the object divisible into at least two object sections, segmenting and classifying the at least two objects and/or the at least two object sections of the object, and determining the immediately upcoming or current workflow step of the intervention. Information relating to objects or object sections relevant to the determined workflow step are retrieved, at least one object of the at least two objects or at least one object section of the at least two object sections of the object is selected taking the information into account, and a collimator of the X-ray device is automatically adjusted for overlaying the selected object or selected object section taking the information into account. At least one X-ray image is acquired and displayed using the thus adjusted collimator.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for automatic actuation of an X-ray device during a medical intervention comprising at least two workflow steps on a body of a patient containing at least two objects, one object that is divisible into at least two object sections, or the at least two objects and the one object that is divisible into the at least two object sections, the method comprising:

acquiring at least one X-ray image of the body containing the at least two objects, the object divisible into the at least two object sections, or the at least two objects and the object divisible into the at least two object sections;

segmenting and classifying the at least two objects, the at least two object sections of the object, or the at least two objects and the at least two object sections of the object;

determining an immediately upcoming or current workflow step of the medical intervention;

retrieving information relating to objects or object sections relevant to the determined immediately upcoming or current workflow step, wherein the information includes an indication of which object or which object sections are relevant to the respective workflow step;

selecting at least one object of the at least two objects or at least one object section of the at least two object sections of the object taking the information into account;

automatically adjusting a collimator of the X-ray device for overlaying the selected at least one object or the selected at least one object section taking the information into account; and acquiring and displaying one or more X-ray images using the adjusted collimator.

2. The method of claim 1, wherein the medical intervention is formed by a robot-assisted navigation.

3. The method of claim 1, wherein the at least one X-ray image and the one or more X-ray images are formed at least to some extent by fluoroscopic X-ray images.

4. The method of claim 1, wherein the objects are formed by instruments, catheters, implants, or guidewires.

5. The method of claim 1, wherein the segmenting and the classifying are performed by at least one machine-learning algorithm.

6. The method of claim 1, wherein the immediately upcoming or current workflow step is determined automatically.

7. The method of claim 6, wherein the immediately upcoming or current workflow step is determined automatically using a machine-learning algorithm or a user query.

8. The method of claim 1, wherein indication of which objects or which object sections are relevant to the respective workflow step is prioritized according to relevance.

9. The method of claim 1, wherein retrieving the information comprises retrieving the information from a memory unit or from a database where the information is stored.

10. The method of claim 9, wherein the information is stored in the memory unit or the database in the form of a list or a lookup table.

11. The method of claim 1, wherein automatically adjusting the collimator of the X-ray device comprises automatically adjusting the collimator of the X-ray device taking the information into account, such that essentially only the at least one relevant object or the at least one relevant object section is inserted.

12. The method of claim 1, wherein automatically adjusting the collimator of the X-ray device comprises automatically adjusting the collimator of the X-ray device taking the information into account, such that a minimum bounding rectangle that contains a whole of the at least one relevant object or the at least one relevant object section is inserted.

13. The method of claim 12, wherein the minimum bounding rectangle is a bounding box.

14. The method of claim 12, wherein the minimum bounding rectangle and an adjustable peripheral region are inserted.

15. The method of claim 1, wherein the method is repeated depending on progress of the medical intervention, at a start of a new workflow step, at regular time intervals, or based on a user-trigger.

16. An X-ray device configured to automatically actuate during a medical intervention comprising at least two workflow steps on a body of a patient containing at least two objects, one object that is divisible into at least two object sections, or the at least two objects and the one object that is divisible into the at least two object sections, the X-ray device comprising:

an acquisition system comprising an X-ray detector and an X-ray source, the acquisition system being configured to acquire X-ray images;

an image processing unit configured to process the X-ray images, the image processing unit having at least one algorithm for segmenting and classifying objects;

a collimator configured to overlay image sections;

a determination unit configured to detect a current or upcoming workflow step;

a calculation unit configured to retrieve information relating to objects relevant to the current or upcoming workflow step, wherein the information includes an indication of which object or which object sections are relevant to the respective workflow step;

a selection unit configured to select at least one object or object section taking the information into account;

an input unit configured to receive user inputs;

a memory unit configured to store data;

a display unit configured to display X-ray images; and a system control unit configured to actuate the X-ray device.

17. The X-ray device of claim 16, wherein the X-ray device is assigned a robotic system comprising at least one robot control unit and a robot-assisted drive system having a drive and a drive mechanism, and wherein the robot-assisted drive system is configured to move at least one medical object in a hollow organ of a patient based on control signals of the at least one robot control unit.

* * * * *